United States Patent [19]

Mitchell et al.

[11] Patent Number: 5,486,233
[45] Date of Patent: Jan. 23, 1996

[54] PIGMENT EXTENDERS

[75] Inventors: Lance S. Mitchell, Mount Hawthorn, Australia; Mary Ann Nordhauser, Franklin Lakes, N.J.; Justin M. Willis, Dalkeith, Australia

[73] Assignee: Western Mining Corporation Limited, Melbourne, Australia

[21] Appl. No.: 141,953

[22] Filed: Oct. 28, 1993

[51] Int. Cl.$^6$ .............................. A61K 7/035; C07C 3/08
[52] U.S. Cl. ..................... 106/416; 106/414; 106/425; 106/429; 106/437; 106/444; 106/447; 106/450; 106/453; 106/460; 106/468; 106/469; 106/471; 106/479; 106/487; 424/69; 424/78.03
[58] Field of Search ..................... 106/414, 416, 106/425, 429, 437, 444, 447, 450, 453, 460, 468, 469, 471, 479, 487; 424/69, 78.03

[56] References Cited

U.S. PATENT DOCUMENTS

| | | | |
|---|---|---|---|
| 4,622,074 | 11/1986 | Miyoshi et al. | 106/419 |
| 4,792,444 | 12/1988 | Fukasawa et al. | 424/63 |
| 4,863,800 | 9/1989 | Miyoshi et al. | 428/403 |
| 4,919,922 | 4/1990 | Miyoshi et al. | 424/63 |
| 5,061,481 | 10/1991 | Suzuki et al. | 424/63 |

Primary Examiner—Mark L. Bell
Assistant Examiner—Scott L. Hertzog
Attorney, Agent, or Firm—Selitto & Associates

[57] ABSTRACT

A pigment composition includes a pigment extender which optionally contains a pigment, and further includes a non-hydrogenated phospholipid material, such as non-hydrogenated lecithin, and a surface modifying agent. Suitable modifying agents are selected from fatty acids, fatty acid esters or fatty acid triglycerides, silicones and mixtures thereof.

22 Claims, No Drawings

PIGMENT EXTENDERS

The present invention relates to pigment and/or pigment extender composition including a phospholipid material, cosmetic compositions including the same, and a process for preparation of such pigment and/or pigment extender compositions.

It is known in the prior art to produce conventional make-up compositions, for example powder, foundation, rouge and the like, to include a water repellant pigment having a surface coated with a silicone or metallic soap. However such pigments still only exhibit moderate water repellancy and are poor in spreadability.

Many attempts have been made in the prior art to overcome the disadvantages described above. For example, it has been proposed to use, in combination with the silicone or metal soap surface treating agents, other oily substances such as mineral oils, animal oils, fatty acids and esters thereof, and paraffin and natural waxes. Whilst some improvement may be achieved in spreadability to a greater or lesser extent, such alternatives exhibit the problems of discoloration and/or evolution of disagreeable odour.

For example, U.S. Pat. No. 4,622,074 to MiyoShi Kasei Co. Ltd. describes the coating of the surface of pigments or extender pigments with hydrogenated lecithin or the reaction product of hydrogenated lecithin and a metal salt, rendering the product hydrophobic.

Similarly, in U.S. Pat. No. 4,863,800 to Miyoshi Easel Co. Ltd., it is suggested to produce a pigment material including a water repellant component together with a saturated fatty acid triglyceride component. Also, in U.S. Pat. No. 4,919,922 to Miyoshi Kasei Co. Ltd. it is suggested to coat the surface of the pigment with a polyolefin containing —COOR groups where R is a metal atom.

Whilst such proposals may provide some improvement in spreadability and feel, the hydrophobicity renders any nurturing value of the phospholipid unavailable to the skin as it is sealed within the hydrophobic casing. Hydrophilicity, on the other hand, would allow the phospholipids or other ingredients access to the surface of the skin. A further advantage of hydrophilic materials is that they often allow for better skin adhesion because of its compatibility with the skin's surface.

Accordingly, it is an object of the present invention to overcome, or at least alleviate, one or more of the difficulties end deficiencies related to the prior art.

Accordingly, in a first aspect there is provided a pigment composition including a pigment extender;

optionally a pigment; and a non-hydrogenated phospholipid material including
  a surface modifying agent selected from the group consisting of fatty acids, fatty acid esters or fatty acid triglycerides, silicones, and mixtures thereof.

The pigment composition according to the present invention most preferably comprises pigment extender which optionally includes a pigment and which is coated with the phospholipid material and modifying agent. The composition may exhibit an improvement in skin adhesion of a cosmetic composition including same. The pigment composition may adhere to the natural moisture of the skin or moisture-created surfaces from base moisturising creams. The pigment composition may also exhibit improved appearance and texture, and does not suffer from undesired odour. As the pigment composition is hydrophilic in nature, its emulsifying activity should be increased.

The pigment composition according to the present invention is also advantageous in that it may be used in a myriad number of cosmetic applications, both of the traditional and modern type. Furthermore, the pigment composition provides the potential for a skin treatment.

The pigment or pigment extender according to this aspect of the present invention may be of an inorganic or organic type. The pigment or pigment extender may be a natural or synthetic material. Examples of pigments include: titanium dioxide, zinc oxide, zirconium dioxide, red iron oxide, yellow iron oxide, black iron oxide, ultramarine blue, Prussian blue, chromium oxide, chromium hydroxide and mixtures thereof.

Examples of pigment extenders include: talc, kaolin, natural and synthetic micas including muscovite mica, sericite, other micas, magnesium carbonate, calcium carbonate, aluminum silicate, magnesium silicate, calcium silicate, synthetic silicates, clay, bentonite, montmorillionite, calcite, chalk, titanated mica, bismuth oxychloride, boron nitride, silica beads, plastic beads such as acrylics, nylons including Nylon 12, natural dyestuffs and mixtures thereof, including tar dyestuff. A talc material is preferred.

A mixture of pigment and pigment extender materials may be used.

The pigment extender and, where present, the pigment most preferably comprises fine powder. Such powder may have an average particle size of approximately 10 µm (by gramulometry) or approximately 4 µm (by Sedigraph determination), as found to be suitable for pigment extender comprising, for example, talc. The powder most preferably is of a relatively narrow size spectrum.

The pigment or pigment extender may be present in the pigment composition in any suitable amounts. The pigment extender may be present in amounts of from approximately 70 to 99.9% by weight, based on the dry weight of the pigment composition. Preferably the pigment extender is present in amounts of from approximately 90 to 99.4% by weight, more preferably approximately 95 to 97.5% by weight.

The pigment may be present in amounts of 0 to approximately 25% by weight, preferably approximately 5 to 10% by weight, based on the dry weight of the pigment composition.

The phospholipid material in the pigment composition according to this aspect of the present invention may be of any suitable type. A phosphatidylcholine, phosphatidylethanolamine, phosphatidylinositol and phosphatidyl serine or mixtures thereof may be used. A lecithin material is preferred, while the lecithin most preferably has a high phospholipid content. The lecithin material may be produced from a natural or synthetic source. A lecithin material refined from naturally occurring lecithin found in any suitable vegetable matter, for example soya bean, egg, corn or rapeseed mat be used.

In general, the lecithin material may be or at least substantially comprise commercially available lecithin of various grades suitable for use in a cosmetic composition. The lecithin product also may be or at least substantially comprise the specific compound identified as lecithin.

The lecithin material may include phosphatidylcholine together with other phospholipids and neutral fat. It has surprisingly been found that a non-hydrogenated lecithin may be used in the composition the subject of the present invention. It is unnecessary to hydrogenate the lecithin to avoid the development of unpleasant odour. Also the emulsifying activity of the lecithin provides a suitable carrier for other compounds, including other phospholipids, and makes them more available to the skin than does a hydrophobic material.

The phospholipid material may be present in any suitable amounts. The phospholipid material may be present in an amount of from approximately 0.1 to 30% by weight, based on the dry weight of the pigment composition, preferably approximately 0.25 to 7.5% by weight, more preferably approximately 0.75 to 5% by weight.

Accordingly, in a preferred aspect there is provided a pigment composition including approximately 70 to 99.9% by weight, based on the dry weight of the pigment composition of a pigment extender selected from the group consisting of talc, kaolin, natural and synthetic micas, other micas, magnesium carbonate, calcium carbonate, aluminum silicate, magnesium silicate, calcium silicate, clay, bentonite, montmorillionite, calcite, chalk, titanated mica, bismuth oxychloride, boron nitride, silica heads, plastic beads such as acrylics, nylons, natural dyestuffs and mixtures thereof;

0 to approximately 25% by weight of a pigment selected from the group consisting of titanium dioxide, zinc oxide, zirconium dioxide, red iron oxide, yellow iron oxide, black iron oxide, ultramarine blue, Prussian blue, chromium oxide, chromium hydroxide and mixtures thereof; and approximately 0.1 to 30% by weight of a non-hydrogenated phospholipid material treated with a surface modifying agent selected from the group consisting of fatty acids, fatty acid esters or fatty acid triglycerides, all suitable and cosmetically approved silicones, dimethicones, cyclomethicones, teflon, and mixtures thereof.

The surface modifying agent may include oleic, palmitic, stearic, linoleic or linolenic acid, or mixtures thereof. The fatty acid esters may include, or be selected from the group consisting of, isocetyl stearate, diisopropyl dimerate, neopentanoate, isocetylstearyl stearate, isopropyl isostearate, diisostearyl dilinoleate octadecyl palmitate, and mixtures thereof. For example, isocetyl stearyl stearate and diisopropyl dimerate have been found to be suitable.

The triglycerides may include, or be selected from the group consisting of, caprylic acid, caprylic/capric triglycerides, caprylicycapric linoleic acid, dicaprylate, dicaprate, hydrogenated palm oil, hydrogenated coconut oil, glyceryl stearate, cocoglycerides or hydrogenated soybean oil.

The silicones may include, or be selected from the group consisting of, dimethicone, simethicone, cyclomethicone and mixtures thereof. The silicone component may be provided in the form of a liquid, wax or gum.

Desirably the surface modifying agent may include a fatty acid ester component, optionally together with a fatty acid, triglyceride or silicone component, vitamins such as vitamin E or A, all proteins such as lauroyl lysine, leucine or any suitable protein for treatment of the skin.

The products produced can vary, with the selection of surface modifying agent or mixture thereof, in transparency, texture, hydrophilicity, binding capability, emulsifying capability, oil absorption, treatment to the skin, etc. The resulting formulas are quite stable, have good ageing characteristics, and little odour. Depending upon the surface modifying agent used, the stability of the product will be equal to or better then products produced from using hydrogenated lecithins.

The surface modifying agent may be present suitable effective amounts. The surface modifying agent may he present in amounts of from approximately 0.05 to 10% by weight, based on the dry weight of the pigment composition, preferably approximately 0.1 to 2.5% by weight, more preferably approximately 0.1 to 1% by weight.

The pigment compositions according to the present invention may be prepared in any suitable manner. Desirably, the pigment composition may be prepared utilising a relatively small amount of solvent.

Accordingly, in a further aspect of the present invention there is provided a process for preparing a pigment composition as described above, which process includes providing
    a pigment extender;
    optionally a pigment
    a non-hydrogenated phospholipid material;
    a surface modifying agent selected from the group consisting of fatty acids, fatty acid esters, fatty acid triglycerides, silicones or mixtures thereof; and
    an aqueous or organic liquid;

forming a dispersion or solution of the phospholipid material with the liquid;

adding the surface modifying agent to the dispersion or solution so formed;

mixing the modified dispersion or solution with the pigment extender and optionally the pigment; and subjecting the modified pigment extender to a drying step.

In a preferred aspect, the phospholipid material includes a lecithin material. The phospholipid material may be mixed with water to form an aqueous dispersion. The surface modifying agent may be added to the aqueous dispersion of phospholipid material in any suitable manner and in any suitable order. Desirably, the phospholipid material is added to water at approximately room temperature, and is mixed vigorously using a high speed dispersing machine until the phospholipid material is completely dispersed. The surface modifying agent can then be added to the dispersion.

In an alternative aspect, the surface modifying agent may be added to the pigment extender before the addition of the phospholipid material.

The dispersion step may be conducted at room temperature or at temperatures up to approximately 80° C. if desired, to aid in the dispersion process.

In an alternative aspect, the liquid is an organic liquid such as an organic alcohol. The organic alcohol may be selected from methanol, ethanol, isopropyl alcohol or mixtures thereof. In this aspect, the phospholipid material is solubilised in the organic liquid. The solution may be formed at elevated temperature, but below the boiling point of the liquid. However a liquid with a low boiling point is preferred as this aids in the drying step discussed below.

In the mixing step according to the process of the present invention, the dispersion or solution formed as discussed above is added to the dry pigment/pigment extender and vigorously mixed such that the dispersion or solution thoroughly contacts the surface of the pigment/pigment extender. The mixing process may be conducted at approximately room temperature.

Desirably the pigment or extender material is a talc material, the phospholipid material is a lecithin material and the surface modifying agent is a fatty acid eater.

The treated pigment so formed is then subjected to a drying step. The drying step may be conducted in any suitable manner. The drying step may he conducted at temperatures of approximately 50° to 80° C., preferably approximately 55° to 70° C. The drying step may be conducted in a drying oven. In a preferred aspect, the treated pigment/pigment extender may be treated by using high temperature steam to heat an external jacket in order to achieve the drying step.

The product so formed may be in the form of a dry powder.

If desired, the product may be subjected to a disaggregation stage, such as a crushing or grinding step, to break down any agglomerates which form on drying. For example where talc is used as the pigment extender, the talc may be treated in a high shear mixer to achieve disaggregation.

In a further aspect of the present invention, there is provided a cosmetic composition including a pigment extender;

optionally a pigment; and a non-hydrogenated phospholipid material including
a surface modifying agent selected from the group consisting of fatty acids, fatty acid esters or fatty acid triglycerides, silicones, and mixtures thereof.

The cosmetic composition may include any standard compounding ingredients normally used in the preparation of cosmetics. Various other additives may be included into the cosmetic composition including: sunscreen agents, softening agents, hydrating agents (sorbitol, glycerine), cicatrisive agents, anti-free radical agents, perfumes and the like. The cosmetic composition may include a supplementary component selected from the group consisting of vitamins such as Vitamin E. acetate etc., other phospholipids such as phosphatidylethanolamine, proteins such as lauroyl lysine, or leucine, triglycerides which may act as additional binder systems and/or texture producing vehicles.

The cosmetic composition may take the form of a powder including a pressed powder, foundation, lipsticks, liquid foundation, rouge, eye shadow or the like.

The present invention will now be more fully described with reference to the accompanying examples. It should be understood, however, that the description following is illustrative only, and should not be taken as a restriction on the generality of the invention described above.

EXAMPLE 1

To 50 g of water add 8 g of lecithin and stir vigorously at room temperature until the lecithin is well dispersed.

To the lecithin dispersion add 1.6 g of isocetyl stearate and continue mixing until well dispersed.

Add 98.25 g of talc to a laboratory blender, e.g. Waring, and pour in 11.1 g of prepared emulsion.

Mix contents at low speed to achieve a good mixture before continuing blending at high speed.

Dry the powder in an oven (75°–80° C.) for at least 2 hours.

The dried talc is placed in a high speed mixer to break up agglomerates formed and produce a fine powder having an average particle size of approximately 10 μm (by granulometry) or 4μm (by Sedigraph).

The Phospholipid content is 64% of the coating while the fatty acid content is 36%. The resulting formula is quite stable, with excellent aging properties, excellent slip characteristics and a creamy texture with good adhesion properties and spreadability. The coating is a 1.75% addition onto an extremely pure talc substrate resulting in a high brightness product with minimal "yellowing" effect.

The properties of the talc, which essentially also are applicable to the resultant coated product, are set out below:

| Mineralogy by XRD | | |
| --- | --- | --- |
| Talc | 98 | % |
| Asbestiform (CTFA J4-1) | 0 | % |
| Dolomite | <1 | % |
| Magnesite | <1 | % |
| Chemical Analysis by XRF (Unmodified) | | |
| $SiO_2$ | 62,1 | % |
| MgO | 32,1 | % |
| $Fe_2O_3$ | <0.1 | % |
| CaO | 0.2 | % |
| MnO | 0.2 | % |
| $Al_2O_3$ | <0.01 | % |
| Heavy Metals (USPXXII) | <40 | ppm |
| Fluoride (FCC) | <20 | ppm |
| Optical Properties | | |
| Reflectance (G.E.) | 91,5 | % |
| Refractive Index | 1,57 | |
| Chemical Properties | | |
| Loss on Ignition 1000°, 60 min (unmodified) | 5,1 | % |
| Loss on Ignition 1000°, 60 min (modified) | 6,8 | % |
| pH 10% Dilution | 8,5 | |
| Physical Properties | | |
| Moisture (110° C.) | <0,2 | % |
| Bulk Density (CTFA C8-1) | 0,45 | g/cm$^3$ |
| Tapped Density (CTFA C7-1) | 0,69 | g/cm$^3$ |
| Hardness (Mohs) | 1 | |
| Density | 2,7 | g/cm$^3$ |
| Particle Size Distribution | | |
| Sedigraph 5100 (unmodified) | | |
| <16.5 μm | 98% | |
| <10 μm | 92% | |
| <5 μm | 65% | |
| <2 μm | 22% | |
| Median Particle Size (d50) 3.8 μm | | |

EXAMPLE 2

Mix 1.4 ml of diisopropyl dimerate with 1.25 ml of methanol by drawing solutions into a 5 ml syringe. Shake syringe vigorously.

Add emulsion slowly from the syringe to 15 g lecithin while mixing.

Place contents into water bath (65° C.) and stir mixture. Continue until the mixture is sufficiently fluid to pour.

Add sufficient of lecithin dispersion to 98.25 g of talc (in waring blender) to achieve required lecithin loading.

Mix contents at low speed and then at high speed.

Place talc in oven at 75° to 80° C. for 60 minutes.

Finally, it is to be understood that various other modifications and/or alterations may be made without departing from the spirit of the present invention as outlined herein.

We claim:

1. A powdered pigment composition for application to the skin including finely divided, hydrophobic pigment extender particles; and optionally finely divided, hydrophobic pigment particles;

and wherein the pigment extender particles and optional pigment particles are coated by a coating of non-hydrogenated, amphiphilic, lecithin phospholipid material, and a surface modifying agent selected from the group consisting of fatty acids, fatty acid esters, fatty acid triglycerides, and mixtures thereof, said coating having a weight percent composition of greater than 50% phospholipid material, said coated pigment extender having an increased hydrophilicity permitting said phospholipids to be adsorbed by the skin of a user.

2. A pigment composition according to claim 1, including approximately 70 to 99.9% by weight, based on the dry weight of the pigment composition of a pigment extender selected from the group consisting of talc, kaolin, natural and synthetic micas, magnesium carbonate, calcium carbonate, aluminum silicate, magnesium silicate, calcium silicate, clay, bentonite, montmorillionite, calcite, chalk, titanated mica, bismuth oxychloride, boron nitride, silica beads, acrylic beads, nylon beads, natural dyestuffs and mixtures thereof;

0 to approximately 25% by weight of a pigment selected from the group consisting of titanium dioxide, zinc oxide, zirconium dioxide, red iron oxide, yellow iron oxide, black iron oxide, ultramarine blue, Prussian blue, chromium oxide, chromium hydroxide and mixtures thereof; and approximately 0.1 to 30% by weight of a non-hydrogenated amphiphilic, lecithin phospholipid material coated with a surface modifying agent selected from the group consisting of fatty acids, fatty acid esters or fatty acid triglycerides, silicones, and mixtures thereof.

3. A pigment composition according to claim 2, wherein the pigment extender includes a talc.

4. A pigment composition according to claim 2, wherein the non-hydrogenated phospholipid material is coated with approximately 0.05 to 10% by weight of a surface modifying agent.

5. A pigment composition according to claim 4, wherein the surface modifying agent includes a fatty acid ester component optionally together with a fatty acid, triglyceride, and/or silicone component.

6. A pigment composition according to claim 5, wherein the fatty acid ester is selected from the group consisting of isocetyl stearate, diisopropyl dimerate, neopentanoate, isocetylstearyl stearate, octadecyl palmitate, and mixtures thereof.

7. A process for preparing a powdered pigment composition, which process includes (A) providing
a finely divided, hydrophobic pigment extender;
optionally a finely divided, hydrophobic pigment;
a non-hydrogenated, amphiphilic lecithin phospholipid material;
a surface modifying agent selected from the group consisting of fatty acids, fatty acid esters, fatty acid triglycerides, or mixtures thereof; and
an aqueous or organic liquid;

(B) forming a dispersion or solution of the phopholipid material with the aqueous or organic liquid at room temperature;

(C) adding the surface modifying agent to the dispersion or solution so formed at room temperature;

(D) adding the pigment extender and optional pigment to the dispersion or solution at room temperature such that the dispersion or solution thoroughly contacts the surface of the pigment extender and optional pigment;

(E) subjecting the resulting dispersion or solution to a drying step; and (F) deagglomerating the dried pigment composition.

8. A process according to claim 7, wherein the pigment extender includes a talc.

9. A process according to claim 8, wherein the surface modifying agent includes a fatty acid ester selected from the group consisting of isocetyl stearate, diisopropyl dimerate, neopentanoate, isocetylstearyl stearate, octadecyl palmitate, and mixtures thereof.

10. A process according to claim 7, wherein the phospholipid material is mired with water to form an aqueous dispersion, and the surface modifying agent is added to the dispersion so formed.

11. A process according to claim 7, wherein the phospholipid material is liquified in an organic liquid, and the surface modifying agent is added to the mixture.

12. A process according to claim 9, wherein the drying step is conducted at temperatures of approximately 50° C. to 80° C.

13. A cosmetic composition including a pigment composition as claimed in claim 1.

14. A cosmetic composition according to claim 13, including approximately 70 to 99.9% by weight, based on the dry weight of the pigment composition of a pigment extender selected from the group consisting of talc, kaolin, natural and synthetic micas, magnesium carbonate, calcium carbonate, aluminum silicate, magnesium silicate, calcium silicate, clay, bentonite, montmorillionite, calcite, chalk, titanated mica, bismuth ozychloride, boron nitride, silica beads, acrylic beads, nylon beads, natural dyestuffs and mixtures thereof;

0 to approximately 25% by weight of a pigment selected from the group consisting of titanium dioxide, zinc oxide, zirconium dioxide, red iron oxide, yellow iron oxide, black iron oxide, ultramarine blue, Prussian blue, chromium oxide, chromium hydroxide and mixtures thereof; and approximately 0.1 to 30% by weight of a non-hydrogenated amphiphilic, lecithin phosphlipid material coated with a surface modifying agent selected from the group consisting of fatty acids, fatty acid esters or fatty acid triglycerides, silicones, and mixtures thereof.

15. A cosmetic composition according to claim 13, wherein the pigment extender includes a talc.

16. A cosmetic composition according to claim 13, further including a supplementary component selected from the group consisting of vitamins, other phospholipids, and other triglycerides.

17. A process for preparing a powdered pigment composition, which process includes (A) providing
a finely divided, hydrophobic pigment extender;
optionally a finely divided, hydrophobic pigment;
a non-hydrogenated, amphiphilic, lecithin phospholipid material;
a surface modifying agent selected from the group consisting of fatty acids, fatty acid esters, fatty acid triglycerides, silicones or mixtures thereof; and
an aqueous or organic liquid;

(B) forming a mixture of the pigment extender and the optional pigment and the surface modifying agent at room temperature;

(C) forming a dispersion or solution of the phospholipid material in the aqueous or organic liquid at room temperature;

(D) mixing the mixture of step (B) with the dispersion or solution of step (C) such that the surface modifying agent and the phospholipid material thoroughly contact and coat the surface of the pigment extender and optional pigment;

(E) subjecting the resulting mixture to a drying step to remove the aqueous or organic liquid; and (F) deagglomerating the dried pigment composition.

18. A process according to claim 17, wherein the pigment extender includes talc.

19. A process according to claim 18, wherein the surface modifying agent includes a fatty acid ester selected from the group consisting of isocetyl stearate, diisopropyl dimerate, neopentanoate, isocetylstearyl stearate, octadecyl palmitate, and mixtures thereof.

20. A process according to claim 17, wherein the phospholipid material is mixed with water to form an aqueous dispersion, and the surface modifying agent is added to the dispersion so formed.

21. A process according to claim 17, wherein the phospholipid material is liquified in an organic liquid, and the surface modifying agent is added to the mixture.

22. A process according to claim 19, wherein the drying step is conducted at temperatures of approximately 50° C. to 80° C.

* * * * *

UNITED STATES PATENT AND TRADEMARK OFFICE
CERTIFICATE OF CORRECTION

PATENT NO. : 5,486,233
DATED : January 23, 1996
INVENTOR(S) : Mitchell et al.

It is certified that error appears in the above-indentified patent and that said Letters Patent is hereby corrected as shown below:

```
Column 1, line  2, delete "composition" and insert --compositions--.
          line 26, delete "Easel" and insert --Kasei--.
          line 44, delete "end" and insert --and--.
Column 2, line 52, delete "mat" and insert --may--.
Column 3, line 62, after "present", insert --in any--.
          line 63, delete "he" and insert --be--.
Column 6, line 48, delete "waring" and insert --Waring--.
```

In the Claims

```
Column 7, line 51, delete "phopholipid" and insert --phospholipid--.
Column 8, line  5, delete "mired" and insert --mixed--.
          line 33, delete "phosphlipid" and insert --phospholipid--.
```

Signed and Sealed this

Twentieth Day of August, 1996

Attest:

BRUCE LEHMAN

Attesting Officer     Commissioner of Patents and Trademarks